United States Patent [19]

Gruber et al.

[11] 4,367,217

[45] Jan. 4, 1983

[54] DIPYRICAMOLE SUSTAINED RELEASE FORMS COMPRISING LACQUER-COATED PARTICLES AND THE PREPARATION THEREOF

[75] Inventors: Peter Gruber, Biberach; Rolf Brickl, Warthausen; Gerhard Bozler, Biberach; Herbert Stricker, Ingelheim am Rhein, all of Fed. Rep. of Germany

[73] Assignee: Boehringer Ingelheim GmbH, Ingelheim am Rhein, Fed. Rep. of Germany

[21] Appl. No.: 221,834

[22] Filed: Dec. 31, 1980

[30] Foreign Application Priority Data

Jan. 12, 1980 [DE] Fed. Rep. of Germany ....... 3000979

[51] Int. Cl.$^3$ .......................... A61K 9/22; A61K 9/26; A61K 9/48
[52] U.S. Cl. .......................................... 424/19; 424/20; 424/21; 424/22; 424/32; 424/33; 424/35; 427/3
[58] Field of Search ................................... 424/19–22, 424/32, 33, 35; 427/3

[56] References Cited

U.S. PATENT DOCUMENTS

| | | | |
|---|---|---|---|
| 2,853,420 | 9/1958 | Lowey | 424/20 |
| 2,928,770 | 3/1960 | Bardani | 424/35 |
| 3,081,233 | 3/1963 | Enz et al. | 424/35 |
| 3,247,066 | 4/1966 | Micosovich | 424/35 |
| 3,344,029 | 9/1967 | Berger | 424/35 |
| 3,538,214 | 11/1970 | Polli et al. | 424/35 |
| 3,775,537 | 11/1973 | Lehmann et al. | 424/21 |
| 3,835,221 | 9/1974 | Fulberth et al. | 424/35 |
| 3,917,813 | 11/1975 | Pedersen | 424/35 |
| 3,954,959 | 5/1976 | Pedersen | 424/20 |
| 4,083,949 | 4/1978 | Benedickt | 424/35 |
| 4,193,985 | 3/1980 | Bechgaard et al. | 424/35 |

FOREIGN PATENT DOCUMENTS

| | | |
|---|---|---|
| 64533 | 7/1975 | Australia . |
| 877706 | 1/1980 | Belgium . |
| 2415490 | 10/1974 | Fed. Rep. of Germany . |
| 2336218 | 2/1975 | Fed. Rep. of Germany . |
| 2223047 | 10/1974 | France . |
| 2353285 | 12/1977 | France . |
| 2390959 | 12/1978 | France . |
| 1468172 | 3/1977 | United Kingdom . |
| 1469133 | 3/1977 | United Kingdom . |
| 1479655 | 7/1977 | United Kingdom . |
| 2025227 | 1/1980 | United Kingdom ................. 424/35 |
| 2039737 | 8/1980 | United Kingdom ................. 424/21 |

*Primary Examiner*—Shep K. Rose
*Attorney, Agent, or Firm*—Hammond & Littell, Weissenberger and Muserlian

[57] ABSTRACT

This invention relates to a composition for the sustained release of dipyridamole which comprises (i) spheroid particles comprised of dipyridamole or crystallized salts thereof and pharmacologically acceptable acid or acid substance, and (ii) a coating surrounding said spheroid particles, said coating being comprised of from about 50 to 100 percent by weight of acid-insoluble lacquers soluble in intestinal juices and from about 0 to 50 percent by weight of lacquers insoluble in gastric and intestinal juices and said coating being present in an amount of from about 3 to 30 percent by weight, based on the weight of the spheroid particles, and to the preparation of such a composition.

39 Claims, 6 Drawing Figures

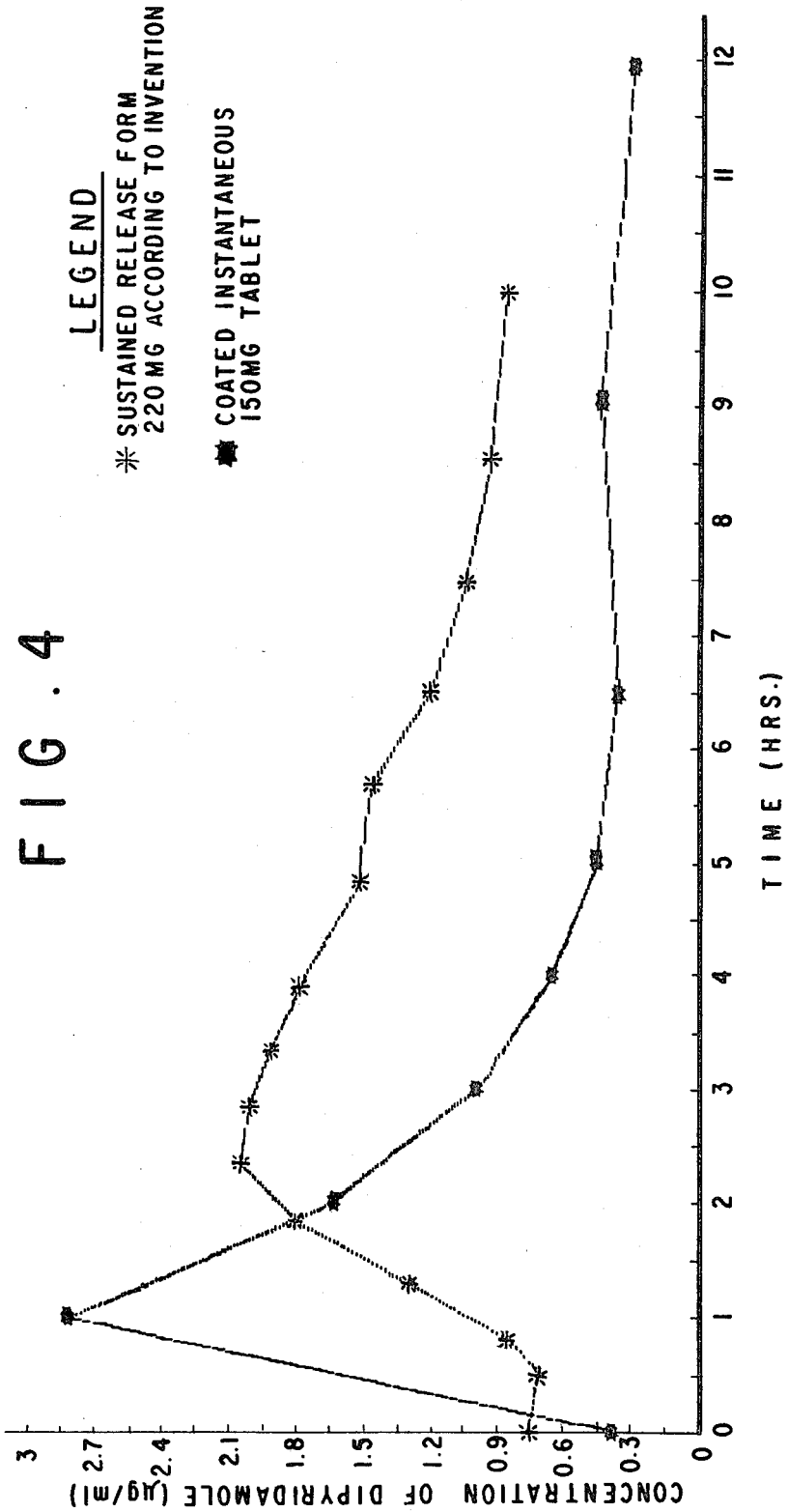

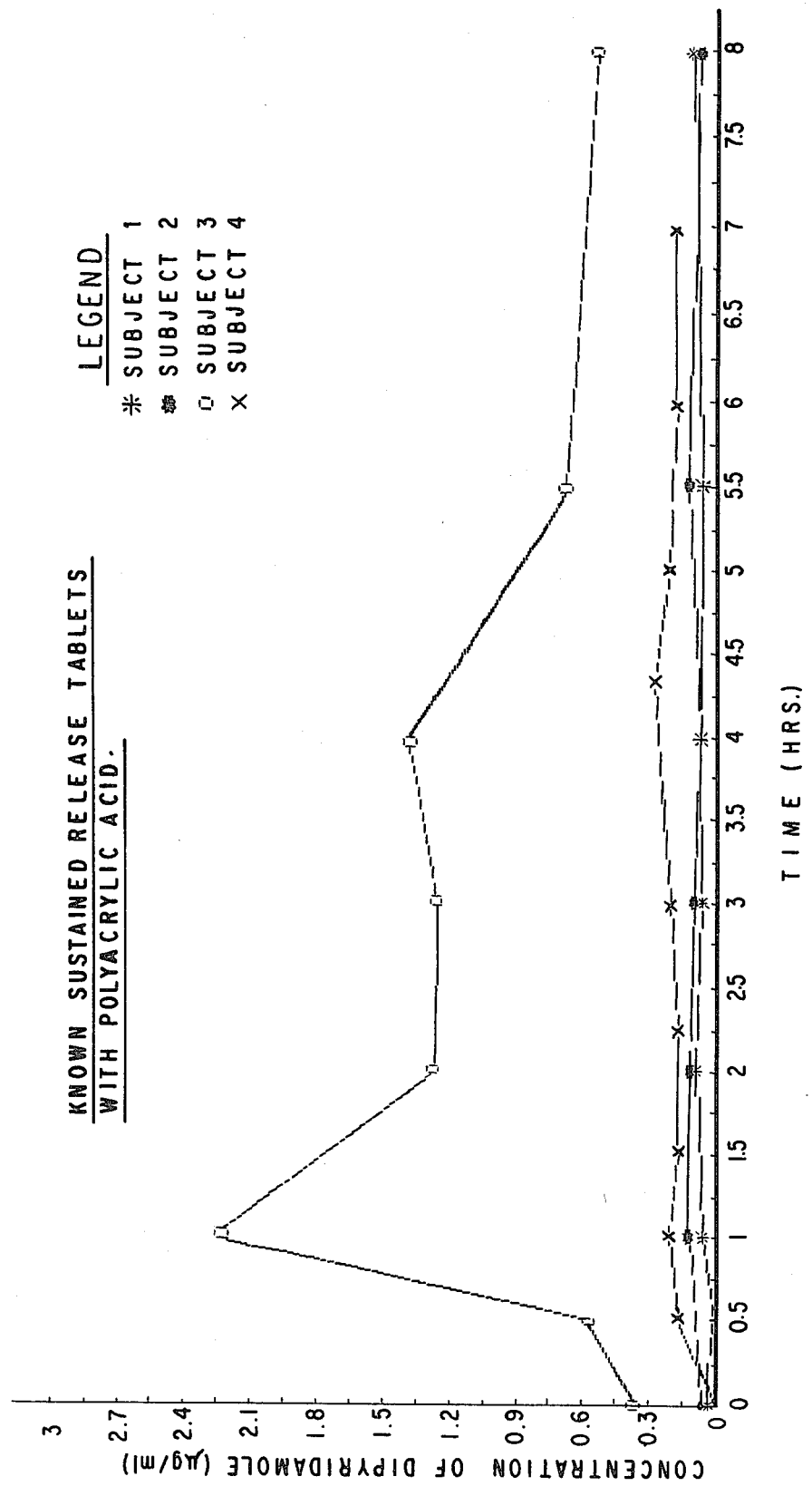

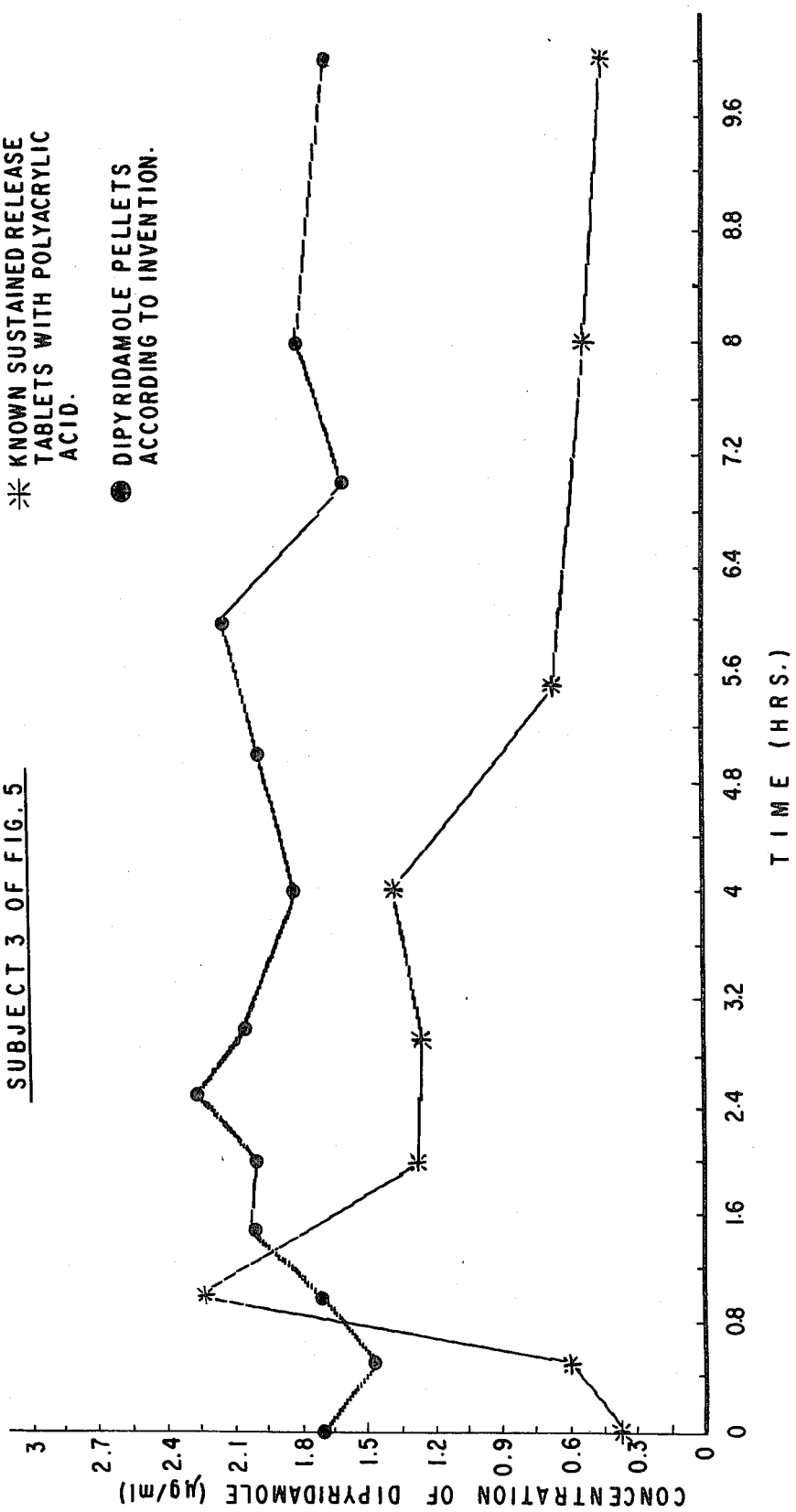

DIPYRICAMOLE SUSTAINED RELEASE FORMS COMPRISING LACQUER-COATED PARTICLES AND THE PREPARATION THEREOF

FIELD OF THE INVENTION

This invention relates to vehicles for the sustained release of dipyridamole. More specifically, this invention relates to spheroid particles provided with a coating and containing dipyridamole and to the preparation of such particles.

BACKGROUND OF THE INVENTION

The compound 2,6-bis(diethanolamino)-4,8-dipiperidinopyrimido-[5,4-d]-pyrimidine, known as dipyridamole, is disclosed in U.S. Pat. No. 3,031,450, incorporated herein by reference. This compound has been successfully used as an active substance, such as a coronary vasodilator, for many years. The nature of the diseases or conditions treated with dipyridamole generally necessitates long-term or constant treatment. At the present time, dipyridamole is administered in tablets or capsules which are readily assimilable, that is, instantaneous, and must be administered three or four times a day.

A sustained release form of administration of dipyridamole would have the advantage of facilitating a reduction in the number of administrations per day, which would lead to better patient compliance. This is of significant importance with regard to long-term medication. Another advantage would be that delayed resorption would lead to more uniform levels in the blood, thus avoiding or minimizing blood level peaks, which can cause deleterious side effects, and would avoid sub-therapeutic levels of active substance, such as can occur with instantaneous forms during longer dosage intervals, for example, during the night. In other words, safety, compatability, and effectiveness of the preparation can be increased. Due to the obvious advantages of a sustained release form of dipyridamole, there have been previous efforts to develop such a form.

In the case of active substances which do not inherently have "sustained release properties" (for example, long biological half life or slow dissolution of crystalline active substances), sustained release forms can be obtained by, for example, the following known methods:

1. The active substance together with excipients is formulated so that it is released slowly, for example, by embedding it in a matrix which does not dissolve or dissolves only slowly; or
2. The active substance together with the excipients is shaped into tablets, pellets, or the like, which are then provided with an insoluble coating which results in a slow release of the active substance.

Furthermore, coating agents for solid medicaments are known which consist of a cellulose derivative soluble in the intestine and of a cellulose derivative insoluble in digestive fluids, these components being present respectively in a mixture ratio of from 30 to 70 percent by weight to from 70 to 30 percent by weight, relative to one another. (See, for example, German Pat. No. 2,415,490.) Also known are oral sustained release forms with a linear release of active substance in the gastrointestinal tract containing spheroid medicament particles which are provided with a dialysis membrane, as is disclosed in German Patent Application (DE-AS) No. 2,336,218. The membrane comprises (i) 15 to 70 percent by weight of a cellulose ether which is insoluble in the pH range of the gastro-intestinal tract and which is not decomposable enzymatically, with an alkoxy group content of from 43 to 50 percent by weight, and (ii) from 85 to 30 percent by weight of one or more compounds soluble only in the alkaline range of the intestinal tract, with a content of from 5 to 40 percent by weight of free carboxyl groups, such as, for example, hydroxypropyl methylcellulose phthalate.

In general, the following prerequisites apply to an active substance for the development of a sustained release form:

good pH-independent solubility in the entire gastrointestinal tract, and no change in the resorption rate in the resorbable part of the gastro-intestinal tract.

However, the physical and biochemical properties of dipyridamole are completely unsuitable for the typical development of a sustained release form. The biological half-life of dipyridamole is relatively short, that is, existing levels in the blood drop quickly, and a uniform dipyridamole level in the blood can be obtained only if active substance is constantly resorbed. Also, dipyridamole is soluble in aqueous medium only in the acid range; more specifically, above a pH of 4 the substance is practically insoluble in water. This means that dipyridamole can be dissolved only in the upper gastro-intestinal tract and consequently resorbed, whereas at the higher pH values occurring in the intestinal region it remains insoluble and is not resorbed.

Since the passage time through the stomach and the upper intestinal regions (with sufficiently acid pH) is relatively short (from about 0.5 to 2 hours), it is therefore difficult to achieve resorption over several hours. Moreover, the residence period in the stomach and in the various intestinal sections can vary considerably. Thus, naturally, in the case of a substance whose solubility depends on the pH, inter-individual and intra-individual variations of levels of active substance in the blood are extremely large when the substance preparation has a slow release, as is necessary with sustained release forms. Further, even if dipyridamole is introduced in dissolved form into various intestinal sections, the resorption rate decreases from the duodenum to the colon.

For the reasons above, the person skilled in the art would consider that an effective sustained release form of dipyridamole was precluded. This situation is also indicated by the presently known "sustained release forms" for dipyridamole. For example, one known form corresponding to known method 1 above comprises a sustained release form in which dipyridamole is pressed into matrix tablets with a swelling polyacrylic acid known by the tradename of Carbopol ®. Determination of release in vitro has shown that this is a completely unsuitable sustained release form of dipyridamole since, with this form, dipyridamole can be dissolved only as long as the tablet is located in the acid medium of the stomach. When the matrix tablet reaches the small intestine, the release of active substance and, consequently the resorption, practically cease.

A recent sustained release form of dipyridamole in pellets, corresponding to known method 2, is described in French Patent Application No. 75 28462. The active substance is applied to inert starter cores which are subsequently provided with a sustained release coating. This publication discloses that pellets prepared according to the Eurand process, that is, enclosing pellets with a polymer coating, are suitable for providing a dipyridamole sustained release preparation. Testing has shown that with use of such pellets the levels of dipyridamole in the blood are distinctly lower in the beginning, as compared to the levels resulting from commercial, instantaneous forms such as coated tablets, and do not persist any longer. Hence, with use of such sustained release pellets, the release of active substance is impaired by about one-half with regard to relative bioavailability.

Thus, all hitherto known sustained release forms of dipyridamole have proven to be completely unsuitable, although in the case of other active substances very useful sustained release forms can be provided with the technologies employed. With the known sustained release forms, no more dipyridamole is dissolved out of the preparation after entry into the small intestine as a result of the increase in the pH value, the resorption of the active substance ceases, and it is impossible to achieve the desired long-lasting blood levels.

OBJECTS OF THE INVENTION

It is an object of the invention to provide vehicles for the sustained release of dipyridamole.

It is also an object of the invention to provide spheroid particles having a coating and containing dipyridamole, said particles being intended for oral administration whereby active substance is released in a controlled and sustained manner in the gastro-intestinal tract.

These and other objects of the invention will become more apparent in the discussion below.

BRIEF DESCRIPTION OF THE DRAWINGS

FIG. 4 represents a comparison of the release characteristics of an instantaneous form and of a sustained release form according to the invention.

FIG. 5 represents the release characteristics of a known type of sustained release form.

FIG. 6 represents a comparison of the release characteristics of a known type of sustained release form and of an embodiment of the invention.

Figure 1:
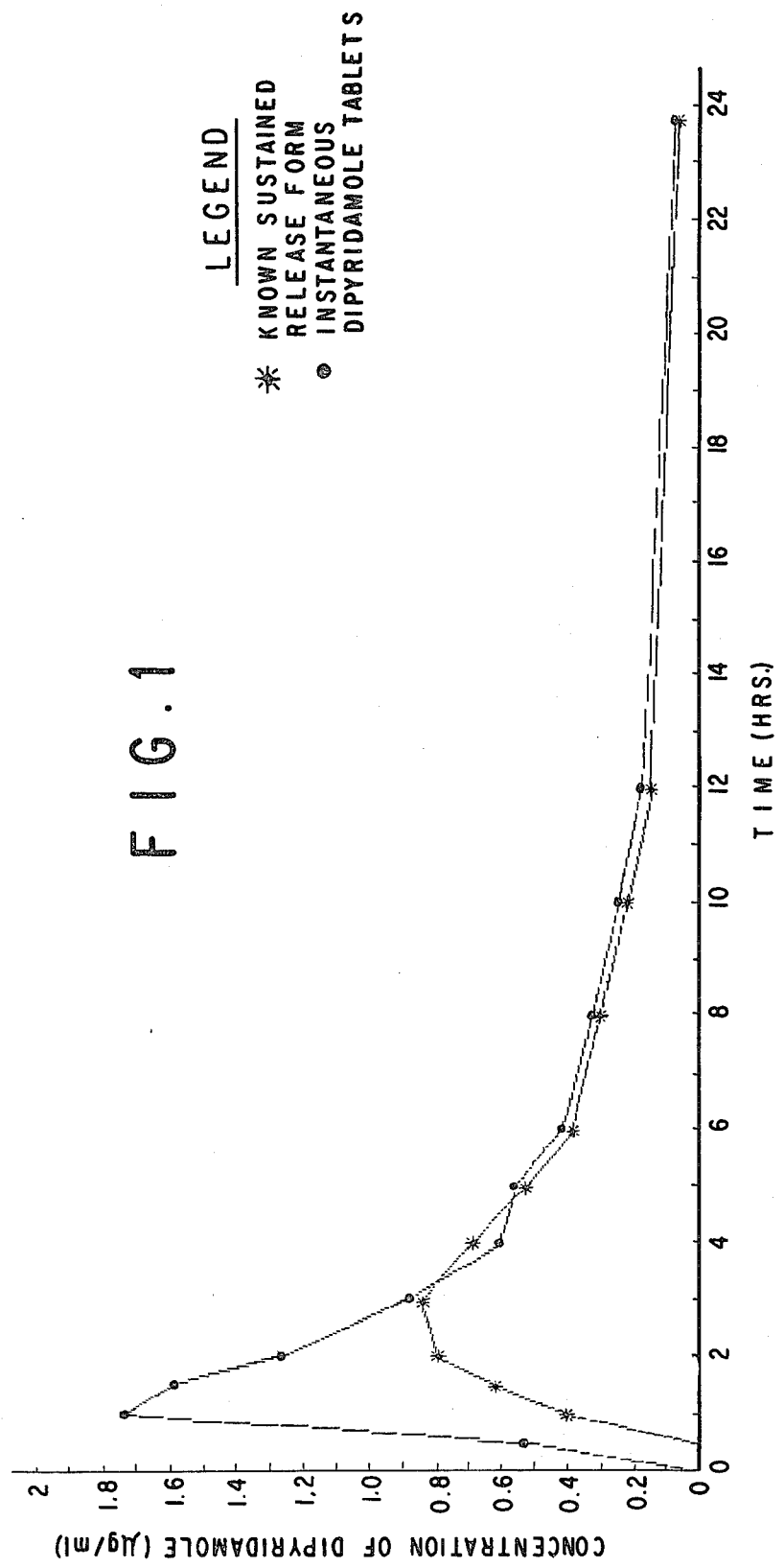
FIG. 1 represents a comparison of the release characteristics of an instantaneous form and of a known type of sustained release form.

These release characteristics are shown by blood-level-curves.

DETAILED DESCRIPTION OF THE INVENTION

Applicants have developed a dipyridamole sustained release form which fully adjusts to the special properties of dipyridamole, which does not have the above-mentioned disadvantages of known sustained release forms for dipyridamole, and which provides a long-lasting level of dipyridamole in the blood. This development has been achieved by a novel combination of different concepts and techniques concerning pharmaceutical preparations.

The following principles were applied:

1. The insolubility of dipyridamole at a higher pH value in lower intestinal sections is compensated by the addition of acidifying substances.
2. Dipyridamole and acid substance are incorporated into particles having a membrane which prevents a rapid neutralization of the acid substance by intestinal juices present in large excess and which retains the acid substance, which dissolves much more quickly, for a sufficiently long time.
3. The particles formed form dipyridamole and acid substance are surrounded with a membrane which exhibits a release characteristic especially adapted to dipyridamole, as is described more fully below.

The dipyridamole sustained release form of the invention consists essentially of a series of spheroid particles of equal or different particle size, each comprised of dipyridamole or acid addition salts of dipyridamole and of acid or acid substances, for example, organic edible acids, the total amount of acid addition salts present and acid or acid substances being in a ratio of at least 1 acid equivalent to 1 mol of dipyridamole, the spheroid particles being surrounded by a dialysis membrane which consists essentially of acid-insoluble lacquers soluble in intestinal juices, the membrane coating comprising from about 3 to about 30 percent by weight, based on the weight of the spheroid uncoated particles. The acid proportion can be substantially higher, for example, up to 30 acid equivalents; however, a proportion of from about 3 to 10 acid equivalents is preferred. The dialysis membrane permits a pH-dependent control of release of dipyridamole.

To produce the spheroid particles, dipyridamole is, for example, mixed and granulated with the acid or acid substances, for example, organic edible acids such as citric acid or tartaric acid, in accordance with the ratios specified above. After the addition of excipients such as lactose and magnesium stearate, the granulate can be pressed to curved cores with, for example, a diameter of about 2 mm. However, the spheroid particles can also be present in the form of larger crystals with a spheroidal shape, when, for example, acid addition salts of dipyridamole are used, in the form of rounded granulates, or in the form of small beads, that is, pellets. Such forms are produced by processes known per se. Small pellets having a diameter of from about 0.1 to 3 mm, preferably of from about 0.8 to 1.5 mm, are preferred.

Suitable acids and acid substances include a plurality of toxicologically harmless, that is, pharmacologically acceptable, acids such as, for example, fumaric acid, malic acid, tartaric acid, citric acid, succinic acid, ascorbic acid, or mixtures of any of these acids as well as pharmacologically acceptable acid substances such as acid salts selected from the group consisting of, for example, sodium or potassium hydrogen sulphate, betaine hydrochloride, or the monosodium or monopotassium salts of tartaric acid or citric acid, and mixtures thereof. Starter cores for the spheroid particles can be comprised of the acids or acid substances described above, of other pharmacologically acceptable acids or acidifying substances, or of conventional pharmaceutically acceptable inert material such as sugar, sugar alcohols, or the like. The acids or acid substances in the starter core can be different from the acids or acid substances admixed with the dipyridamole. Moreover, the acid component of the mixture to be applied to the cores can consist of several of the above-mentioned acids and/or acid substances. Especially suitable for the starter cores are those acids or acid substances which have an approximately spherical shape, for example, tartaric acid, citric acid, malic acid, succinic acid, ascorbic acid, sodium or potassium hydrogen sulphate, monosodium or monopotassium salts of polybasic acids, and betaine hydrochloride.

The ratio of dipyridamole to acid or acid substances must be selected so that a complete release of the dipyridamole is provided. The release is also dependent upon the type of coating used, as is discussed in more detail below.

As mentioned above, the particles or pellets are produced by processes known per se, for example, by means of an apparatus according to the Merumeriza process from acid or acid substance and dipyridamole powder with the aid of adhesive solutions. The preparation is also effected, for example, with the use of a pelleting plate or of wet mixing appliances with special agitator arms. However, the pellets are preferably produced by applying the active substance to starter cores which consist either of conventional inert materials or suitable acids or acid substances, in the presence of a bonding agent.

The use of acids or acid substances for the starter core has two special advantages. First, the degree of dipyridamole to be preferably applied in sustained release forms is from about 150 to 250 mg per dose, and, since an approximately equal quantity by weight of acid or acid substance is appropriately necessary, this dose can be introduced into one still easily swallowable capsule only if dipyridamole plus acid or acid substance make up from about 90 to 95 percent of the crude pellet. This is not possible when inert materials are used. And second, the central acid core, which is then surrounded by a dipyridamole/acid or acid substance mixture, facilitates the otherwise very difficult complete release of dipyridamole.

Suitable bonding agents include adhesive solutions such as starch paste, sugar syrup, and solutions of gelatin, guar rubber, cellulose ether (for example, methylethyl-, hydroxyethyl-, or hydroxypropylmethyl- cellulose), or polyvinylpyrrolidone.

In a preferred preparation method, rounded starter cores of tartaric acid with an average diameter of from about 0.3 to 1 mm, preferably from about 0.5 to 0.7 mm, are sprayed uniformly with an alcoholic polyvinylpyrrolidone solution in a suitable vessel and are mixed with a mixture of 80 parts by weight of dipyridamole and 20 parts by weight of tartaric acid until the balls, that is, the particle cores, roll freely again. After drying, this operation is repeated until the desired total amount of active substance has been applied. The dipyridamole pellets obtained have a size of from about 0.9 to 1.2 mm and preferably consist of at least 95 percent by weight of active substance and acid in a ratio of from about 1.0:1.1. However, it is also possible to dissolve or suspend the active substance in the adhesive solution and to apply this solution or suspension uniformly onto the surface of the starter cores.

Comprehensive in vitro and in vivo tests have shown that the composition of the lacquer coating is of particular importance. The lacquer sprayed onto the pellets should not dissolve in the resorbable part of the gastro-intestinal tract, and the coating must remain in the intestinal tract until the entire active substance is diffused out. The coating must retain the acid or acid substance present in the core until the dipyridamole located therein is completely dissolved. If the coating is dissolved prematurely or breaks down, the intestinal juices present in large excess penetrate the pellets or spheroids and neutralize the acid or acid substance present therein. Because of the virtual insolubility of dipyridamole in the pH range of the intestine, no more active substance can then be dissolved and resorbed. The acid or acid substance present on the inside of the pellets and which dissolves in the fluid, dissolves, in turn, the dipyridamole and draws this through the membrane of the sustained release pellet. Due to an increase in permeability of the coating in the intestinal tract, acid active substance solution is increasingly released into the lower regions of the intestinal tract as the pellet progresses.

In vitro release tests with artificial intestinal juices having a pH of 6.0 to 7.0 show that the active substance dipyridamole diffuses out of the coated sustained release forms, although dipyridamole is practically insoluble at a pH above 4. Obviously, the intestinal juices are buffered by the acid after penetration into the sustained release form. Despite the intestinal juices surrounding the sustained release form, which juices have a pH of from 6.0 to 7.0, an acid medium prevails within the sustained release form, as a result of which the dipyridamole can be dissolved and diffused outwards in dissolved form. Dissolved resorbable dipyridamole is therefore released continuously into the intestinal tract.

It was surprising and unforeseeable that dipyridamole leaving the preparation would remain resorbable in this form over a long time, although, for example, even micronized dipyridamole introduced into the intestinal juices is not resorbed. The cause of this unexpected effect could either be a long-lasting over-saturation by dipyridamole of the intestinal juices, which is also to be observed in vitro, or that the dipyridamole precipitates with its molecules dispersed and is available for resorption in this finely distributed form.

Since dissolved dipyridamole is resorbed especially quickly immediately after leaving the stomach in the uppermost intestinal section, which can lead to high blood level peaks, while, on the other hand, the resorption rate decreases distinctly in the lower intestinal sections, these circumstances necessitate a sustained release coating which first delays the active substance and then releases it in an accelerated manner.

These criteria require a new type of dialysis membrane which is adapted specially to the unusual properties of dipyridamole and which permits a certain pH-dependent control of release. The composition of the coating is selected so that it exhibits a delay of release in the pH range up to 4.5 and an accelerating release of active substance as the pH value rises. The residence time of medicaments and the pH value in the stomach and in the various intestinal sections differ sharply, however, from person to person and in one and the same person at different times. Too large a pH dependence of the release would therefore result in large differences in levels of active substance in the blood over time. However, if the total dose is divided into hundreds of independent, small, sustained release forms, then a statistically uniform, largely consistent passage of this sustained release form through the gastro-intestinal tract is provided. The effects of the differences in the pH gradient and the gastro-intestinal motility of individual patients on the dipyridamole blood level behavior are thereby largely compensated for. Realization of the principle of a certain pH-dependent control of release therefore necessitates in the case of dipyridamole the use of spheroid particles such as rounded granulates or pellets. As discussed more fully below, it has been possible to prove this need in vivo by a comparison of the levels of dipyridamole in the blood after administration of some cores or of pellets with the same coating type.

The dialysis membrane surrounding the individual spheres primarily, that is, up to 100 percent by weight, consists of lacquers soluble in intestinal juices. For example, coating compositions comprised of from about 50 to 90 percent by weight of a methacrylic acid/methacrylate copolymer (acid number of 180 to 200), known by the tradename Eudragit S ®, available from Rohm & Haas, and from about 50 to 10 percent by weight of hydroxypropylmethylcellulose phthalate, known by the tradename HP 55 ®, available from Shinetsu Chem. Comp. Tokyo, have proven especially advantageous. A solution such as, for example, a from about 10 to 15 percent solution of both components in a suitable solvent such as acetone/isopropanol (1:1) or acetone/ethanol (1:1), is used for spraying the spheroids. Although such a coating consists only of components supposedly soluble in intestinal juices, the coating surprisingly does not dissolve in the resorbable part of the intestinal tract. The fact that such coatings are possible at all and are even especially suitable in this case is suprising for two reasons:
1. It is stated in German Pat. No. 2,415,490 that at least 30 percent, preferably at least 40 percent, of the coating constituents must be insoluble in acid and intestinal juices to produce a coating stable in intestinal juices.
2. It was not foreseeable that with such a high proportion of acid-insoluble lacquer a release would take place at all, since acid is constantly dissolved on the inside and is diffused through the membrane.

Suitable components for the lacquer coating include, in addition to those previously mentioned, cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate, and methacrylic acid/methacrylate copolymer (acid number 300 to 330, also known as Eudragit L ®, available from Rohm & Haas), either alone or in admixture.

A certain proportion of the lacquers soluble in intestinal juices can also be replaced by lacquers insoluble in the stomach and in the intestine, without the optimally acting sustained release form thereby suffering very much in its effect. Suitable as such lacquers are ethylcellulose, as well as lacquer substances based on acrylate or methacrylate, such as lacquers which are known by the tradenames Eudragit retard S ® and Eudragit retard L ®, available from Rohm & Haas. The lacquer components insoluble in acid and in intestinal juices may be present in amounts up to about 50 percent, preferably up to about 30 percent by weight.

As shown in Example VIII below, the release of dipyridamole which is first attenuated and then accelerates in lower sections of the intestinal tract, can also be achieved by a successively formed coating. Thus, a coating consisting of 14 percent by weight of ethyl cellulose and 86 percent by weight of hydroxypropylmethylcellulose phthalate can be sprayed with a coating consisting of, for example, cellulose acetate phthalate for further attenuation of the release of dipyridamole in the stomach and upper intestinal tract.

If, however, the proportion of lacquer components soluble in intestinal juices is too small, that is, if it drops below 50 percent by weight, then the release of dipyridamole from the sustained release pellets or particles is unsatisfactory. This is shown by the released quantities measured in vitro for dipyridamole (see, also, Examples IX and X below) and the levels of active substance in the blood determined in vivo which have a poor bioavailability ($<70\%$ relative to an instantaneous form). The cause of this poor release could be that the acid diffuses too quickly through the membrane. However, without acid or acid substance in the pellets no more active substance can be dissolved and diffused through the membrane due to the insolubility of the dipyridamole in a non-acid medium. Either the proportion of lacquer component soluble in intestinal juices must be increased or the acid starter core used in the production of the granulate or pellet must be first sprayed with a solution of a lacquer component soluble in intestinal juices, for example, with a solution of cellulose acetate phthalate or a lacquer combination of Eudragit retard S ® and Eudragit S ® (in a ratio such as of 1:1) and the dipyridamole is subsequently applied to the retarded acid starter core thus treated.

The coatings mentioned according to the invention can contain conventional excipients such as softeners, wetting agents, and dyestuffs. Suitable are pharmacologically acceptable softeners such as, for example, those selected from the group consisting of phthalates, phosphates, glycerol citrate, and polyethylene glycols, glycerol triacetate being preferably used.

The dialysis membrane is applied to the spheroid medicament particles by methods known per se. This can be effected in a rapidly rotating vessel or via the fluidized-bed process by spraying on the lacquer solution forming the dialysis membrane.

The dosage range for the active substance dipyridamole is from about 50 to 500 mg, preferably from about 150 to 250 mg. The spheroid particles prepared according to the above-described processes are filled into, for example, conventional hard gelatin capsules after the particles have been provided with a dialysis membrane. According to this procedure, it is possible to mix pellets or particles of different delay stages and also to optionally add undelayed active substance particles or pellets as a so-called starting dose. However, the dipyridamole sustained-release particles can also be mixed with other pharmaceutical excipients and pressed into tablets. This is possible in the case of particles or pellets with a diameter of up to 1.5 mm, preferably below 1 mm without noticeably damaging the dialysis membrane. After such a tablet is ingested, it disintegrates in a few seconds and, like the capsules, releases the spheroid dipyridamole particles.

The particular difficulty in selecting the optimal acid, the optimal quantity of acid, the optimal coating composition, and the optimal coating thickness has been that these four parameters cannot be varied independently of one another but rather that they influence one another. For this reason, it was not foreseeable to a person skilled in the art that this difficult sustained release preparation could be realized by a combination of different technologies.

The following problems were solved by the discovery of the forms of administration according to the invention:
(1) It was possible to create a situation whereby dipyridamole becomes soluble and independent in its solubility of the pH values of the gastro-intestinal tract.
(2) A diffusion coating was developed which protects the acid or acid substance for hours against premature buffering by the intestinal juices present in large excess. The coating ensures that the dissolved dipyridamole leaves the sustained release pellets completely and that the differences in the dipyridamole resorption rates in the individual sections of the gastro-intestinal tract are compensated for by first a delayed release and then an accelerating release upon further penetration into the lower sections of the intestinal tract. The coating discovered brings about, therefore, a pH-dependent release instead of a linear release of the active substance.

(3) Due to the distribution of the active substance in many hundreds of single sustained release doses, for example, in the form of spheroid particles or pellets or rounded granulates, the effects of different residence times and of the varying pH value in the gastro-intestinal tract on the blood levels are equalized by the statistical distribution of the rates of migration.

The following examples are intended to illustrate the invention and are not to be construed as limiting the invention thereto.

EXAMPLES

Example I

Two hundred kilograms of rounded tartaric acid starter cores of a particle size between 0.6 and 0.8 mm are moistened uniformly in a rotating vessel with a 10 percent alcoholic polyvinylpyrrolidone solution (lower alcohols are suitable for this purpose), whereafter a finely divided mixture of 8 parts by weight of dipyridamole and 2 parts by weight of tartaric acid is scattered therein until the pellets roll freely again. After a short drying phase, adhesive solution is sprayed again, and further powder is then added. Altogether, 300 kg of the powder mixture are applied in this way, about 150 liters of adhesive solution being necessary. The corresponding active substance pellets are between 0.9 and 1.2 mm in size and contain about 46 percent by weight of dipyridamole and 50 percent by weight of tartaric acid. The pellets are dried thoroughly after the final application of powder.

Example II

Two hundred kilograms of non-rounded citric acid starter cores with a particle size of 0.5 to 0.63 mm are coated, under exactly the same conditions as specified in Example I, with 300 kg of a powdered mixture of dipyridamole and citric acid (8:2) to a pellet size of 0.8 to 1.0 mm. The following acids and acidifying substances were also used as starter cores (200 kg in each case): ascorbic acid, malic acid, succinic acid, sodium or potassium hydrogen sulphate, betaine hydrochloride, and monosodium or monopotassium salts of the above-mentioned polybasic organic acids.

Continuing in accordance with the procedure of Example I, mixtures comprised of 8 parts by weight of dipyridamole and 2 parts by weight of tartaric or citric acid or one of the above-mentioned acids or salts, or mixtures thereof, are used. The ratio of the components of the mixture of dipyridamole and acid or acid substance, which mixture is to be applied to the cores can be, in addition to 8:2, 10:0, 9:1, 7:3, 6:4, 5:5, 4:6, 3:7, 2:8, or 1:9. Moreover, in addition to 300 kg of the above-mentioned powder mixtures, the following quantities of the above-mentioned compositions can also be applied to 200 kg of starter cores: 100 kg, 200 kg, 400 kg, 500 kg, or 600 kg. The active substance pellets thus prepared are between about 0.7 and 1.5 mm in size. The ratio of dipyridamole to acid component is between 3:1 (600 kg of dipyridamole to 200 kg of starter cores) and 1:25.

Example III

Fifteen kilograms of dipyridamole powder are mixed with 17 kg of tartaric acid powder in a fluidized-bed granulating appliance. With slow spraying, a structural granulate is produced by means of 25 kg of a 5% hydroxypropylmethyl cellulose solution (methylene chloride/isopropanol). Ninety percent of the dried spherical granulate has a diameter of from 0.6 to 1.0 mm. The content of dipyridamole is about 45 percent by weight. Instead of tartaric acid, citric acid, ascorbic acid, fumaric acid, malic acid, succinic acid, monosodium and monopotassium salts of the above-mentioned polybasic acids, sodium or potassium hydrogen sulphate, or betaine hydrochloride can also be used. The content of dipyridamole can be adjusted to values of 10, 20, 30, 40, 50, 60, or 70 percent by weight by changing the composition of the mixture.

Example IV

Nineteen kilograms of dipyridamole active substance pellets according to Examples I and II are sprayed in a rapidly rotating coating vessel with baffle plates with a solution of

| | |
|---|---|
| Methacrylic acid/methacrylate copolymer (Eudragit S ®) | 675 g |
| Hydroxypropylmethylcellulose phthalate (HP 55 ®) | 675 g | in 8.5 kg of acetone/isopropanel (1:1). One hundred and fifty grams of triacetin are added as softener. The release of active substance is determined by the paddle method of USP XX (100 revolutions per minute). Unless otherwise stipulated, the release is always tested under the following conditions:

| | |
|---|---|
| First hour | pH 2.0 |
| Second hour | pH 4.5 |
| third to seventh hour | pH 6.0 |

The buffering is effected with a saturated $Na_2HPO_4$ solution.

The following release values for dipyridamole are obtained:

TABLE 1

| Time (hours) | Dipyridamole Released (percent by weight) |
|---|---|
| 1 | 5.0 |
| 2 | 23.1 |
| 3 | 48.0 |
| 4 | 63.0 |
| 5 | 75.1 |
| 6 | 84.0 |
| 7 | 89.0 |

Example V

Two hundred seventy-six kilograms of dipyridamole active substance pellets prepared according to Example I are sprayed in a rotating vessel intermittently with a solution of Methacrylic acid/methacrylate copolymer

| | |
|---|---|
| (Eudragit S ®) | 19.92 kg |
| Hydroxypropylmethylcellulose phthalate (HP 55 ®) | 4.08 kg | in 300 kg of acetone/isopropanol (3:7). An amount of 8.16 kg of triacetin is added as softener and 4.08 kg of talcum are added as separating agent.

The following release values for dipyridamole are obtained:
(Rotating basket method, USP XX, 100 revolutions per minute)
1 hour, pH 1.2 (USP gastric juice)
2 to 8 hours, pH 5.5 (phosphate buffer)

TABLE 2

| Time (hours) | Dipyridamole Released (percent by weight) |
|---|---|
| 1 | 5.1 |
| 2 | 22.9 |
| 3 | 42.7 |
| 4 | 54.9 |
| 5 | 64.7 |
| 6 | 74.2 |
| 7 | 82.7 |
| 8 | 90.6 |

Example VI

Nineteen kilograms of dipyridamole active substance pellets prepared according to Example I are sprayed in fluidized-bed apparatus with a solution of

| | |
|---|---|
| Ethylcellulose (ethoxy group content of 48 to 49.5%) | 200 g |
| Copolymer of acrylates and methacrylates (Eudragit retard S ®) | 100 g |
| Methacrylic/methacrylate copolymer (Eudragit S ®) | 100 g |
| Hydroxypropylmethylcellulose phthalate (HP 55 ®) | 1200 g | in 18 kg of acetone/ethanol (1:1). Four hundred grams of triacetin are added as softener.

The following release values for dipyridamole are obtained:

TABLE 3

| Time (hours) | Dipyridamole Release (percent by weight) |
|---|---|
| 1 | 2.9 |
| 2 | 30.0 |
| 3 | 77.6 |
| 4 | 88.5 |
| 5 | 93.0 |

Example VII

Nineteen kilograms of dipyridamole active substance pellets prepared according to Example I are sprayed in a rapidly rotating coating vessel with baffle plates with a solution of

| | |
|---|---|
| Copolymer of acrylates and methacrylates (Eudragit retard S ®) | 200 g |
| Methacrylic acid/methacrylate polymer (Eudragit S ®) | 200 g |
| Hydroxypropylmethylcellulose phthalate (HP 55 ®) | 1200 g | in 14 kg of acetone/isopropanol (1:1). Four hundred grams of triactin are added as softener.

The following release values for dipyridamole are obtained:

TABLE 4

| Time (hours) | Dipyridamole Release (percent by weight) |
|---|---|
| 1 | 2.3 |
| 2 | 14.3 |
| 3 | 50.1 |
| 4 | 70.8 |
| 5 | 79.5 |
| 6 | 88.2 |
| 7 | 93.1 |

Analogously, the following compositions were also sprayed onto the pellets and granulates prepared according to Examples I to III.

| | | |
|---|---|---|
| (a) | Methacrylic acid/methacrylate copolymer (Eudragit S ®) | 80 parts |
| | Triacetin | 20 parts |
| (b) | Copolymer of acrylates and methacrylates (Eudragit retard S ®) | 40 parts |
| | Methacrylic acid/methacrylate copolymer (Eudragit S ®) | 50 parts |
| | Polyethylene glycol 6000 | 10 parts |
| (c) | Copolymer of acrylates and methacrylates (Eudragit retard S ®) | 20 parts |
| | Methacrylic acid/methacrylate copolymer (Eudragit S ®) | 70 parts |
| | Polyethylene glycol 6000 | 10 parts |
| (d) | Methacrylic acid/methacrylate copolymer (Eudragit S ®) | 80 parts |
| | Methacrylic acid/methacrylate copolymer (Eudragit L ®) | 10 parts |
| | Triacetin | 10 parts |
| (e) | Cellulose acetate phthalate | 60 parts |
| | Hydroxypropylmethylcellulose phthalate (HP 55 ®) | 30 parts |
| | Triacetin | 10 parts |
| (f) | Ethylcellulose phthalate | 70 parts |
| | Copolymer of acrylates and methacrylates (Eudragit retard S ®) | 20 parts |
| | Triacetin | 10 parts |
| (g) | Ethylcellulose | 10 parts |
| | Hydroxypropylmethylcellulose succinate | 75 parts |
| | Triacetin | 15 parts |
| (h) | Hydroxymethylpropylmethylcellulose trimellitate | 35 parts |
| | Methacrylic acid/methacrylate copolymer (Eudragit S ®) | 60 parts |
| | Polyethylene glycol | 5 parts |

Example VIII

Two kilograms of dipyridamole active substance pellets prepared according to Example II are sprayed in a rapidly rotating coating vessel with baffle plats with a solution of

| | |
|---|---|
| Ethycellulose (ethoxy group content of 48 to 49.5%) | 28 g |
| Hydroxypropylmethylcellulose phthalate (HP 55 ®) | 172 g | in 1.8 kg of acetone/ethanol (1:1).

The following release values for dipyridamole are obtained:

TABLE 5

| Time (hours) | Dipyridamole Released (percent by weight) |
|---|---|
| 1 | 8.0 |
| 2 | 28.1 |
| 3 | 80.3 |
| 4 | 90.3 |
| 5 | 96.5 |

These pellets are sprayed again with 80 g of cellulose acetate phthalate dissolved in 720 ml of acetone/isopropanol (1:4). The release values are reduced to the following:

TABLE 6

| Time (hours) | Dipyridamole Released (percent by weight) |
|---|---|
| 1 | 4.1 |
| 2 | 17.5 |
| 3 | 35.7 |
| 4 | 55.3 |
| 5 | 65.6 |
| 6 | 77.9 |
| 7 | 86.3 |
| 8 | 91.2 |

Example IX

Two kilograms of dipyridamole pellets according to Example I are sprayed in a rapidly rotating coating vessel with baffle plates with a solution of

| | |
|---|---|
| Copolymer of acrylates and methacrylates (Eudragit retard S ®) | 200 g |
| Copolymer of acrylates and methacrylates (Eudragit retard L ®) | 100 g | in 2.7 kg of acetone/isopropanol (4:6). Thirty grams of dibutylphthalate are added as softener.

The following release values for dipyridamole are obtained:

TABLE 7

| Time (hours) | Dipyridamole Released (percent by weight) |
|---|---|
| 1 | 19.2 |
| 2 | 38.7 |
| 3 | 46.7 |
| 4 | 49.0 |
| 5 | 52.7 |
| 6 | 54.1 |
| 7 | 55.0 |
| 8 | 55.1 |

Example X

Two kilograms of dipyridamole pellets prepared according to Example I are sprayed in a rapidly rotating coating vessel with baffle plates with the solution of

| | |
|---|---|
| Copolymer of acrylates and methacrylates (Eudragit retard S ®) | 180 g |
| Methacrylic acid/methacrylic acid copolymer (Eudragit L ®) | 90 g | in 2.7 kg of acetone/isopropanol (1:1). Thirty grams of triacetin are added as softener.

The following release values for dipyridamole are obtained:

TABLE 8

| Time (hours) | Dipyridamole Released (percent by weight) |
|---|---|
| 1 | 10.4 |
| 2 | 22.5 |
| 3 | 35.8 |
| 4 | 45.1 |
| 5 | 54.2 |
| 6 | 61.1 |
| 7 | 65.0 |
| 8 | 67.2 |

Example XI (a) Two kilograms of rounded tartaric acid starter cores of a particle size of 0.6 to 0.8 mm are sprayed in a rotating vessel with a solution of

| | |
|---|---|
| Methacrylic acid/methacrylate copolymer (Eudragit S ®) | 35 g |
| Copolymer of acrylates and methacrylates (Eudragit retard S ®) | 35 g | in 620 g of acetone/isopropanol (1:1). Ten grams of triacetin are added as softener.

(b) Two kilograms of the covered tartaric acid starter cores prepared as in step (a) are moistened uniformly in a rotating vessel with a 10 percent alcoholic polyvinylpyrrolidone solution, whereupon, analogously to Example I, 3 kg of a powdered mixture of 8 parts of dipyridamole and 2 parts of tartaric acid are applied. Ninety-five percent of the pellets have a particle size of from 0.9 to 1.25 mm, the content of dipyridamole being 45.6 percent by weight and that of tartaric acid being 50.2 percent by weight.

(c) Two kilograms of dipyridamole pellets prepared in step (b) are sprayed in a rotating vessel with a solution of

| | |
|---|---|
| Copolymer of acrylates and methacrylates (Eudragit retard S ®) | 80 g |
| Methacrylic acid/methacrylate copolymer (Eudragit L ®) | 100 g | in 1.8 kg of acetone/isopropanol (1:1). Twenty grams of triacetin are added as softener.

The following release values for dipyridamole are obtained:

TABLE 9

| Time (hours) | Dipyridamole Released (percent by weight) |
|---|---|
| 1 | 8.1 |
| 2 | 27.3 |
| 3 | 52.1 |
| 4 | 64.7 |
| 5 | 74.0 |
| 6 | 81.7 |
| 7 | 88.4 |

Example XII

Two kilograms of covered dipyridamole pellets prepared according to Example IV with a dipyridamole content of 42.0 percent by weight are mixed with 1.5 kg of microcrystalline cellulose, 0.4 kg of corn starch, and 0.1 kg of polyvinylpyrrolidone. After addition of 20 g of magnesium stearate, mixing is continued for a further 5 minutes. Heavy, oblong 7×13 mm tablets having individual weights of 718 mg are pressed from the mixture with a weak applied pressure. The tablets disintegrate in about 45 seconds. The release of dipyridamole is accelerated only insignificantly.

Applicants' invention can perhaps be better appreciated by making reference to FIGS. 1 to 6. FIG. 1 represents a comparison of the blood-levels of an instantaneous form of dipyridamole and of pellets prepared according to the Eurand process, that is, a known sustained release form. Since testing of only one subject would have been of limited value, at best, testing of the release characteristics was conducted with ten adult subjects. Doses of 100 mg were administered, and the levels of active substance in the blood, in μg/ml, were measured over a period of twenty-four hours. The results are set forth in FIG. 1. The randomized cross-over test (sustained release pellets against undelayed dipyridamole coated tablets) shows that the levels in the blood of dipyridamole sustained release pellets are distinctly lower at the beginning in comparison with undelayed commercial form and do not last any longer.

Figure 2:
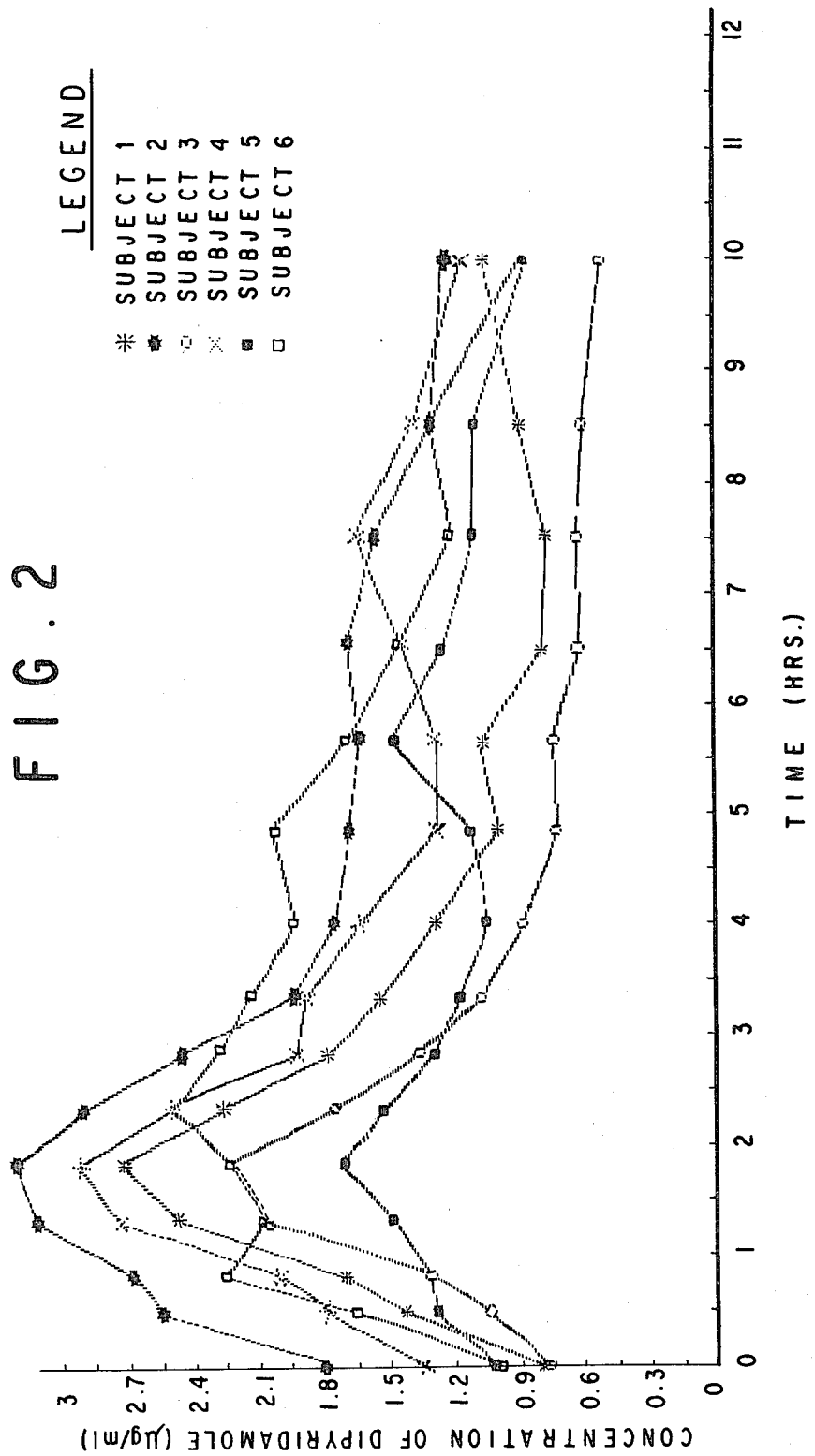
FIG. 2 represents the release characteristics of dipyridamole pellets in a capsule.
Figure 3:
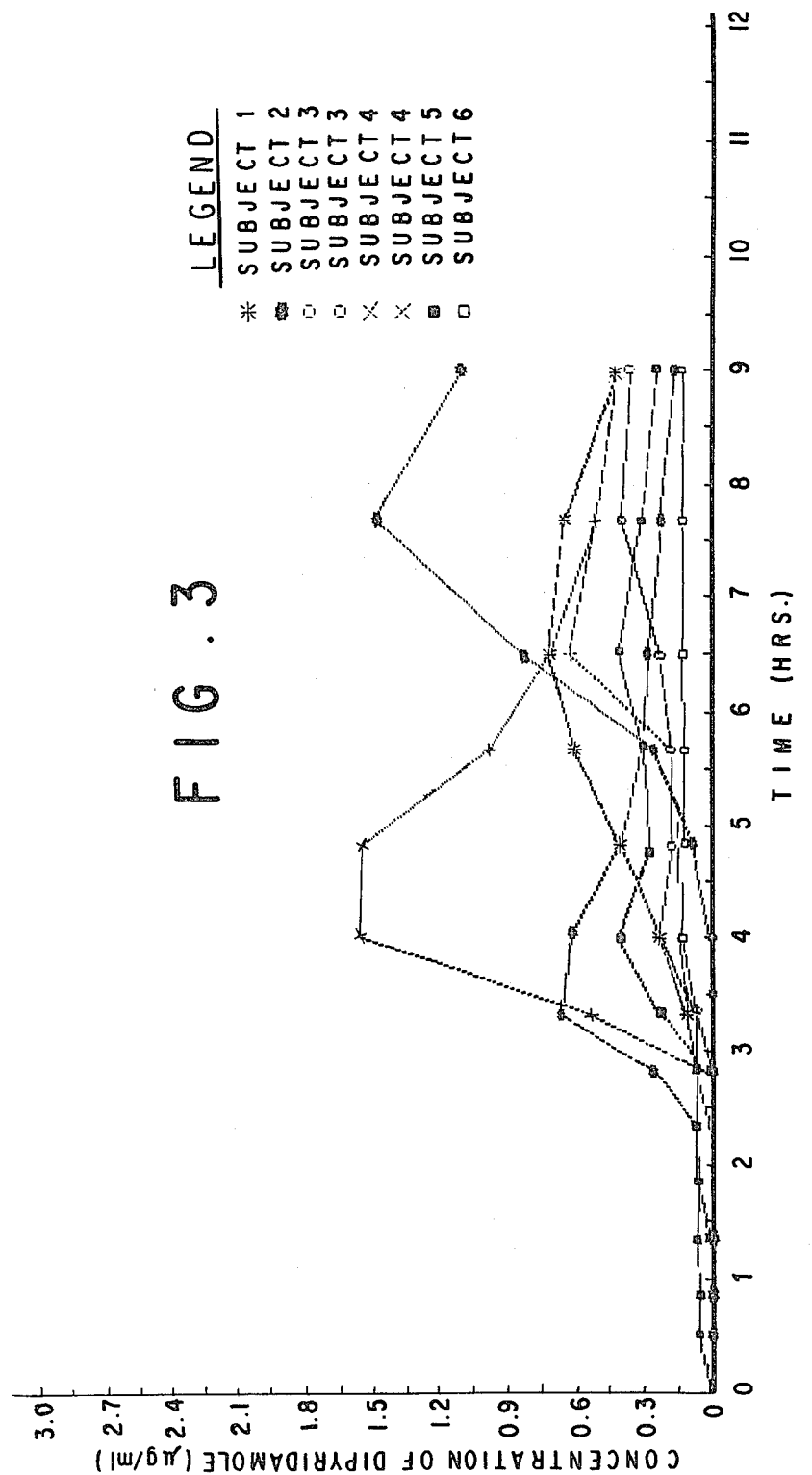
FIG. 3 represents the release characteristics of dipyridamole cores in a capsule.

FIGS. 2 and 3 illustrate the blood levels of six test persons, FIG. 2 showing the dose distributed using several hundred pellets according to the invention filled into a capsule, while FIG. 3 illustrates the use of six cores, diameter of 6 mm, in a capsule. The pellets and cores have the same type of coating. It will be seen that the levels in the blood in FIG. 2 appear much more uniform than in FIG. 3. Moreover, it is also shown in FIG. 3 that levels in the blood of the same test person obtained on different days differ sharply. Furthermore, as is confirmed in part by FIG. 4, where levels of active substance in the blood resulting from use of pellets according to the invention are shown, use of surface area which is obviously substantially larger in the case of pellets leads to significantly higher and longer-lasting levels in the blood.

FIG. 4 indicates how the levels of dipyridamole in the blood are different for the sustained release form described according to the invention and for an instantaneous form. It will be seen that despite the higher dosage of 220 mg with the sustained release form in comparison with 150 mg in the instantaneous form, lower blood level maxima are achieved which are, however, maintained at a high level over several hours. The bioavailability (calculated as an area below the blood level curve) of the new sustained release forms is from about 90 to 110 percent, relative to the instantaneous forms at the same dosage.

FIG. 5 represents the results of in vivo testing of four test persons, each of whom received a dose of 2×200 mg of dipyridamole per day in sustained release tablets comprising polyacrylic acid, as was known. With three test persons, the levels of dipyridamole in the blood were, both with respect of relative bioavailability and blood level maxima, clearly 10 percent below those obtained with the forms mentioned according to the invention, that is, there were complete therapy failures. The third test person had a rather higher, but likewise completely insufficient level in the blood (relative bioavailability about 30 percent which is clearly demonstrated in FIG. 6.). The entirely inadequate and, also, still sharply fluctuating blood levels show that no reliable effectiveness can be expected of this form.

FIG. 6 represents a comparison of the blood levels in the same subject (subject 3 of FIG. 5) after the administration of sustained release tablets comprising polyacrylic acid as was known, and of pellets prepared according to the invention. The pellets provide a much more uniform and sustained release of active substance.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A composition for the sustained release of dipyridamole which comprises (i) spheroid particles comprised of (a) dipyridamole or acid addition salts thereof and (b) at least one pharmacologically acceptable acid or acid substance, the total amount of acid from acid addition salts present and the acid or acid substance being in a ratio of at least 1 acid equivalent to 1 mol of dipyridamole, said particles having a diameter of from about 0.1 to 3 mm, and (ii) a coating surrounding said spheroid particles, said coating being comprised of from about 50 to 100 percent by weight of acid-insoluble lacquers soluble in intestinal juices and from about 0 to 50 percent by weight of lacquers insoluble in gastric and intestinal juices and said coating being present in an amount of from about 3 to 30 percent by weight, based on the weight of the spheroid particles.

2. The composition of claim 1, wherein the spheroid particles contain dipyridamole as component (a) and the acid or acid substance and dipyridamole are present in a ratio of at least 1 acid equivalent to 1 mol of dipyridamole.

3. The composition of claim 2, wherein the ratio is from about 1 to 30 acid equivalents to 1 mol of dipyridamole.

4. The composition of claim 1, wherein the spheroid particles contain acid addition salts of dipyridamole as component (a) and the acid or acid substance and acid addition salts are present in amounts such that the total amount of acid or acid substance and acid from the acid addition salts is in a ratio of at least 1 acid equivalent to 1 mol of dipyridamole.

5. The composition of claim 1, wherein the acid is selected from the group consisting of fumaric acid and tartaric acid.

6. The composition of claim 1, wherein the coating comprises from 0 to about 14 percent by weight of ethylcellulose.

7. The composition of claim 1, wherein the spheroid particles comprise rounded granulates or pellets and have a diameter of from about 0.8 to 1.5 mm.

8. The composition of claim 1, wherein the coating contains lacquers insoluble in gastric and intestinal juices.

9. The composition of claim 1, wherein the acid-insoluble lacquers soluble in intestinal juices are selected from the group consisting of methacrylic acid/methacrylate copolymers (acid number 180 to 200), hydroxypropylmethylcellulose phthalate, cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate, methacrylic acid/methacrylate copolymer (acid number 300 to 330), and mixtures of one or more thereof.

10. The composition of claim 9, wherein the lacquer soluble in intestinal juices comprises from about 90 to 50 percent by weight of methacrylic acid/methacrylate copolymer (acid number 180 to 200) and of from about 10 to 50 percent by weight of hydroxypropylmethylcellulose phthalate.

11. The composition of claim 10 which contains an additional outer coating comprising a lacquer soluble in intestinal juices.

12. The composition of claim 1, wherein the spheroid particles comprise a core consisting essentially of acid or acid substance and said core has a coating of a retarding lacquer component.

13. The composition of claim 1, wherein coated spheroid particles are contained in conventional hard gelatin capsules.

14. The composition of claim 1, wherein the coated spheroid particles have diameters of up to 1.5 mm and are contained with conventional excipients in tablet form.

15. The composition of claim 1, wherein the spheroid particles have cores and the cores are comprised of an acid or acid substance different from the acid or acid substance in admixture with dipyridamole.

16. The composition of claim 1, wherein the acid-insoluble lacquer soluble in intestinal juices is soluble at a pH of about 4.5 or greater.

17. A method for treatment of cardiovascular disorders in a host in need of such treatment which comprises administering to said host a cardiovascularly effective amount of a composition of claim 1.

18. The composition of claim 1, wherein the coating is comprised of 100 percent by weight of acid-insoluble lacquers soluble in intestinal juices.

19. A hard gelatin capsule which contains an effective amount of a composition of claim 1 wherein the dipyridamole or acid addition salts thereof are present in an amount of from about 50 to 500 mg.

20. The capsule of claim 19, wherein the dipyridamole or acid addition salts thereof are present in an amount of from about 150 to 250 mg.

21. A tablet which comprises a compressed mixture of an effective amount of a composition of claim 1, wherein the coated spheroid particles thereof have a particle size of up to 1.5 mm and conventional pharmaceutical excipients and wherein the dipyridamole or acid addition salts thereof are present in an amount of from about 50 to 500 mg.

22. The tablet of claim 21, wherein the dipyridamole or acid addition salts thereof are present in an amount of from about 150 to 250 mg.

23. The method of claim 17, wherein the spheroid particles contain dipyridamole as component (a) of the composition and the acid or acid substance and dipyridamole are present in a ratio of at least 1 acid equivalent to 1 mol of dipyridamole.

24. The method of claim 23, wherein the ratio is from about 1 to 30 acid equivalents to 1 mol of dipyridamole.

25. The method of claim 17, wherein the spheroid particles contain acid addition salts of dipyridamole as component (a) of the composition and the acid or acid substance and acid addition salts are present in amounts such that the total amount of acid or acid substance and acid from the acid addition salts is in a ratio of at least 1 acid equivalent to 1 mol of dipyridamole.

26. The method of claim 17, wherein the acid is selected from the group consisting of fumaric acid and tartaric acid.

27. The method of claim 17, wherein the coating comprises from 0 to about 14 percent by weight of ethylcellulose.

28. The method of claim 17, wherein the spheroid particles comprise rounded granulates or pellets and have a diameter of from about 0.8 to 1.5 mm.

29. The method of claim 17, wherein the coating contains lacquers insoluble in gastric and intestinal juices.

30. The method of claim 17, wherein the acid-insoluble lacquers soluble in intestinal juices are selected from the group consisting of methacrylic acid/methacrylate copolymers (acid number 180 to 200), hydroxypropylmethylcellulose phthalate, cellulose acetate phthalate, ethylcellulose phthalate, hydroxypropylmethylcellulose succinate, cellulose acetate succinate, hydroxypropylmethylcellulose hexahydrophthalate, cellulose acetate hexahydrophthalate, hydroxypropylmethylcellulose trimellitate, methacrylic acid/methacrylate copolymer (acid number 300 to 330), and mixtures of one or more thereof.

31. The method of claim 30, wherein the lacquer soluble in intestinal juices comprises from about 90 to 50 percent by weight of methacrylic acid/methacrylate copolymer (acid number 180 to 200) and of from about 10 to 50 percent by weight of hydroxypropylmethylcellulose phthalate.

32. The method of claim 31 which contains an additional outer coating comprisng a lacquer soluble in intestinal juices.

33. The method of claim 17, wherein the spheroid particles comprise a core consisting essentially of acid or acid substance and said core has a coating of a retarding lacquer component.

34. The method of claim 17, wherein the coating is comprised of 100 percent by weight of acid-insoluble lacquers soluble in intestinal juices.

35. The method of claim 17, wherein coated spheroid particles are contained in conventional hard gelatin capsules.

36. The method of claim 17, wherein the coated spheroid particles have diameters of up to 1.5 mm and are contained with conventional excipients in tablet form.

37. The method of claim 17, wherein the spheroid particles have cores and the cores are comprised of an acid or acid substance different from the acid or acid substance in admixture with dipyridamole.

38. The method of claim 17, wherein the acid-insoluble lacquer soluble in intestinal juices is soluble at a pH of about 4.5 or greater.

39. A process for the preparation of a sustained release dipyridamole composition which comprises the steps of:
  (a) uniformly spraying rounded starter cores having an average diameter of from about 0.3 to 1 mm with an alcoholic polyvinyl pyrrolidone solution;
  (b) mixing the sprayed starter cores from step (a) with a mixture of dipyridamole or acid addition salts thereof and a sufficient amount of acid substance to make the dipyridamole component water-soluble until the starter cores thus treated roll freely;
  (c) drying the treated cores from step (b), steps (a) to (c) being repeated until the treated cores obtain a size of from about 0.1 to 3 mm; and
  (d) applying to the treated cores from step (c) a lacquer coating comprising from about 50 to 100 percent by weight of pharmacologically acceptable acid-insoluble lacquers soluble in intestinal juices and from 0 to about 50 percent by weight of pharmacologically acceptable lacquers insoluble in gastric and intestinal juices, said coating being present in an amount of from about 3 to 30 percent by weight, based on the weight of the spheroid particles.

* * * * *

UNITED STATES PATENT AND TRADEMARK OFFICE
CERTIFICATE OF CORRECTION

PATENT NO. : 4,367,217
DATED : January 4, 1983
INVENTOR(S) : PETER GRUBER et al.

It is certified that error appears in the above-identified patent and that said Letters Patent is hereby corrected as shown below:

Title page, item [54], and Column 1, line 2, in the title "DIPYRICAMOLE" should read -- DIPYRIDAMOLE --.

Title page, item [56], "Micosovich" should read -- Milosovich --

Column 4, line 5, "form" should read -- from --.

Column 5, line 19, "degree" should read -- dosage --.

Column 6, lines 30-31, "resportion" should read -- resorption --.

Signed and Sealed this

Twelfth Day of April 1983

[SEAL]

Attest:

Attesting Officer

GERALD J. MOSSINGHOFF
Commissioner of Patents and Trademarks